United States Patent [19]

Koehler et al.

[11] Patent Number: 4,857,532

[45] Date of Patent: Aug. 15, 1989

[54] COCKROACH GROWTH REGULATING COMPOSITION AND METHOD

[75] Inventors: Philip G. Koehler, Gainesville, Fla.; Richard Kramer, Olney, Md.; Richard S. Patterson, Gainesville, Fla.

[73] Assignee: University of Florida, Gainesville, Fla.

[21] Appl. No.: 189,037

[22] Filed: May 2, 1988

[51] Int. Cl.$^4$ ............................................. A01N 43/90
[52] U.S. Cl. ..................................................... 514/262
[58] Field of Search ......................................... 514/262

[56] References Cited

PUBLICATIONS

Engebretson et al, Comp. Biochem. Physiol., vol. 83B, pp. 93–97 (1986).
The Merck Index, 10th Ed. (1983), p. 273, #273.
Beck et al, Ann. Entomol. Soc. Am., vol. 50, pp. 166–170 (1957).
Gordon, J. Insect Physiol., vol. 14, pp. 41–52 (1968).
Cochran, Ann. Rev. Entomol., vol. 20, pp. 29–49 (1958).
Mullins et al, Nature, vol. 283, pp. 567–569 (1980).

Primary Examiner—Allen J. Robinson
Attorney, Agent, or Firm—Dennis P. Clarke

[57] ABSTRACT

A composition and method for the regulation of the growth and mortality of cockroaches based on the administration thereto of allopurinol.

6 Claims, No Drawings

COCKROACH GROWTH REGULATING COMPOSITION AND METHOD

BACKGROUND OF INVENTION

1. Field of the Invention

The present invention relates to the regulation of growth of insects, more specifically, cockroaches. The U.S. Government has certain rights in the invention described and claimed herein.

2. Description of the Prior Art

Few studies have identified and evaluated the efficacy of nutritional growth inhibitors for cockroaches. The elimination of food and water to facilitate control in pest management has been advocated. Beck et al [Ann. Entomol. Soc. Am., Vol. 50, pp. 166-170 (1957)] reported that 6-methoxybenzoxazolinone, a naturally occurring growth inhibitor found in corn reduced the growth efficiency of German cockroaches. Cycloheximide inhibited protein synthesis, thereby depressing growth, but it had no effect on oxidative metabolic weight loss. On the other hand, veratrine and cocaine severely depressed oxidative metabolic weight loss, while only veratrine depressed growth [Gordon, J. Insect. Physiol., Vol. 14, pp. 41-52 (1968)].

Allopurinol, a structural analog of the natural purine base, hypoxathine is an effective inhibitor of xanthine oxidase, and, therefore, blocks the formation of uric acid, the metabolic end product of purine catabolism in humans. It is presently used in humans to treat gout.

Engebretson et al, Comp. Biochem. Physiol., Vol. 83B, pp. 93-97 (1986) discuss the effects of allopurinol on urate metabolism in the German cockroach.

Cochran [Ann. Rev. Entomol., Vol. 30, pp. 29-49 (1985)] reviewed the interrelationship of three cockroach cell types (trophocytes, mycetocytes and urocytes) within the fat body and the ability of these insects to utilize stored uric acid during periods of nutritional stress. The deposition of paternal urates during copulation and their subsequent incorporation into the ootheca has been reported as an additional function of this metabolic reserve in German cockroaches [Mullins et al, Nature, Vol. 283, pp. 567-569 (1980)].

It is an object of the present invention to provide a novel method and composition for regulating the growth of cockroaches.

SUMMARY OF THE INVENTION

The above and other objects are realized by the present invention which provides a method for regulating the growth of and killing insects by administering thereto a growth regulating amount of allopurinol for a time sufficient to affect the growth and mortality thereof.

A further embodiment of the invention comprises a cockroach bait or attractant formulation containing an insect growth regulating effective amount of allopurinol.

DETAILED DESCRIPTION OF THE INVENTION

The present invention is predicated on the discovery that the ingestion of a certain critical minimum amount of allopurinol by insects, particularly cockroaches, for an extended period of time adversely affects the growth and mortality thereof as well as their ability to reproduce.

It will be understood by those skilled in the art that, for purposes of description of the present invention, the following definitions apply.

The terms, "bait" and "attractant", refer to any formulation to which insects, e.g. cockroaches, are attracted and which they will ingest. Such compositions are well known to those skilled in the art and it will be understood that any such material which is inert with respect to allopurinol may be employed in the practice of the invention. Reviewed suitable foods and compounds to incorporate into toxic baits, generally, carbohydrates such as grain products, powdered sucrose, 1-arabinose, dehydrated potatoes, or maltose, have been used in baits. Saturated fatty acids and alcohols have increased feeding activity in cockroaches. [M. K. Rust, 1986, Managing Household Pests In Advanves in Urban Pest Management (Burnett, G. W., and J. M. Owens, Ed.) Van Nostrand Reinhold Co., pp. 335-368].

The term "administering", as employed herein is intended to include any treatment or method which makes the administered material available to cockroaches for ingestion. Thus, "administering" would include such steps as providing in an area known to be frequented by the insects a composition adapted for attracting, and to be ingested by cockroaches, containing allopurinol.

The term "growth regulating amount", will be understood by those skilled in the art to refer to any amount of allopurinol which, when ingested by an insect, affects the rate of growth and eventually kills the insect.

Although the invention is described in detail referring to examples employing German cockroaches, it will be understood that the invention is applicable to any species of cockroach or other insects.

Generally, the bait or attractant should contain from about 0.05 to about 2.0%, by weight, of allopurinol. Optimally, the allopurinol is administered to the cockroaches to be killed for a period of time of at least about 5 weeks, although less time may be effective to achieve desired results in some cases.

EXAMPLE 1

Baits were formulated (w/w) by dissolving or suspending allopurinol in 15 ml of acetone and mixing this solution with a sufficient amount of powdered 20% casein or ground laboratory chow to make 25 g of bait. Control baits were formulated by mixing the dry bait material with acetone. Acetone was evaporated from the baits, which were then ground to a fine powder and stored at 4° C. until used.

An initial screening of a 2% allopurinol bait on second and third stage nymphs of German cockroaches is shown in Tables 1 and 2. Feeding nymphs 2% allopurinol baits resulted in reproduction failure, and all males died within 1-21 days postemergence, with most dying within 1-7 days. Emergent females were observed for a 9 week period and although many produced "false" oothecae, the oothecae appeared shriveled or darkened on the protruding end, and all were dropped or failed to hatch.

Feeding postemergent, unmated males 2% allopurinol bait for 3 days or continuously during the reproductive cycle led to a reduction in the number of nymphs produced per female. Postemergent adult exposure to allopurinol produced the following results: 3-day feeding—4 nymphs/female, continuous feeding—1 nymph/female, control—24 nymphs/female.

TABLE 1

The effect of 2% allopurinol bait on
survival of third stage German cockroach nymphs

| Weeks postexposure | Percent survival | |
|---|---|---|
| | Allopurinol | Control |
| 0 | 100 | 100 |
| 1 | 92 | 89 |
| 2 | 89 | 86 |
| 3 | 86 | 82 |
| 4 | 83 | 81 |
| 5 | 75 | 81 |
| 6 | 47 | 81 |
| 7 | 39 | 80 |
| 8 | 29 | adults |
| 9 | 22 | — |
| 10 | 13 | — |
| 11 | 11 | — |
| 12 | 7 | — |

TABLE 2

The effect of 2% allopurinol bait on
survival of second stage German cockroach nymphs

| Weeks postexposure | Percent survival | |
|---|---|---|
| | Allopurinol | Control |
| 0 | 100 | 100 |
| 1 | 96 | 95 |
| 2 | 90 | 93 |
| 3 | 82 | 91 |
| 4 | 76 | 90 |
| 5 | 66 | 86 |
| 6 | 51 | 84 |
| 7 | 33 | 83 |
| 8 | 16 | 82 |
| 9 | 3 | 82 |
| 10 | 2 | 81 |

To determine the effect of allopurinol on total body urates, uric acid analyses were made on German cockroaches at various developmental times. The results are set forth in Table 3. Nymphs fed allopurinol bait failed to accumulate uric acid, whereas in untreated individuals uric acid accumulates with age. However, feeding allopurinol to 14-day old adults did not remove accumulated uric acid from their bodies.

TABLE 3

Effect of allopurinol on total body
uric acid in adult German cockroaches

| Age (days) of Cockroaches | Mean uric acid content ($\mu$g/mg) | | | |
|---|---|---|---|---|
| | Allopurinol | | Control | |
| | Males | Females | Males | Females |
| 1 | 8.87 | — | 106.3 | 83.1 |
| 30 | — | 9.79 | 88.4 | 91.0 |
| 30 (14 days fed untreated bait, 16 days treated bait) | 161.3 | 133.90 | — | — |

EXAMPLE 2

Bait compositions according to the following formalities were prepared according to Example 1.

Preliminary studies were conducted by placing 50 third instar nymphs (17–24 days old) in a 1-gallon utility jar the upper lip of which was greased with a mixture of equal parts mineral oil and petrolatum. The jar contained two corrugated cardboard harborages, a plastic water bottle and a paper souffle cup filled with the appropriate bait. Tests were conducted at 25±1 C., 50±1% RH, and a photoperiod of 8:16 (L:D).

Mortality and the total group weight of all surviving cockroaches were recorded at weekly intervals. As adult emergence occurred, the number of males, females, nymphs and ootheca were recorded. Each test was replicated at least twice and was terminated when hatch or total mortality occurred.

Allopurinol was evaluated as a bait in 20% casein, as well as standard laboratory rodent chow using a 2.0% (w/w) concentration. The effect of this compound on reproduction in 1-2 day old postemergent adults was studied by feeding unmated adults (25-30 females and 10 males) a 2.0 percent bait in 20% casein, either 72 hours or continuously. Allopurinol was evaluated as a 2.0% bait in conjunction with 0.1% hydroprene residual treatments. Choice tests were also conducted, as above, using a 2.0% bait in laboratory rodent chow. Two-week old mated adults (50 females and 50 males) were given a choice of 2.0% bait or untreated lab chow to determine if postemergence exposure would affect hatch. Linear regression equations were used to determine if the percent survival of treated populations/week was affected by exposure to allopurinol.

Uric acid analyses were used to determine the effects of allopurinol on German cockroach total body urates. Analyses were performed on penultimate nymphs, emergent adults (1 day old), postemergent adults and adults which had been continuously fed allopurinol bait during their development. Mean values were determined and analyzed for significance ($P=0.05$) using the Waller-Duncan method (SAS Institute, 1985).

Nymphs fed allopurinol bait exhibited delayed and asynchronous adult emergence 5 weeks posttreatment and total mortality occurred during week 13. Controls had a more synchronous emergence at 4–5 weeks; however, survival on the 20% casein diet was reduced to 45%. The percent survival of the population fed 0% casein at 5 weeks was 30%, while survival in the allopurinol population was 47%. In contrast to the treated populations, the 0% casein population had emergent adults which produced 1 viable ootheca. A similar study was conducted on second instar nymphs and produced comparable results, except that percent survival was reduced ca. 6%, and longevity of allopurinol and 0% casein fed nymphs was extended 2 weeks.

EXAMPLE 3

Allopurinol was formulted as a 2% w/w concentration in laboratory rodent chow and the above experiments repeated. In comparing the results of allopurinol as a casein bait and as a laboratory rodent chow bait, there was no significant difference in the percent survival during the studies, with the exception of a 1 week delay in the onset of survival decline in the latter population. The combination of bait and a 0.1% hydroprene residual treatment apparently did not affect the efficacy of either compound. An allopurinol choice test indicated no appreciable difference in percent survival (2% at 10 weeks) of the population given a food choice and the percent survival (6% at 10 weeks) of those provided the no choice casein diet.

Feeding nymphs 2% allopurinol baits resulted in reproductive failure; all males died within 1–21 days postemergence (most within the first seven days). Emergent females were observed for a 9 week period and although many produced "false" ootheca, they appeared shriveled or darkened on the protruding end, and all were either dropped or failed to hatch.

Feeding postemergent unmated adults 2% allopurinol bait for 3 days or continuously during the reproductive cycle resulted in a reduction in the number of nymphs/female. Postemergent adult exposure to allopurinol produced the following results: 3 day feeding—4 nymphs/female, continuous feeding—1 nymph/female and control—24 nymphs/female. Reproduction occurred in two-week old mated adults provided a choice of baits, however, no attempt was made to determine the number of nymphs/female.

EXAMPLE 4

To determine the effect of allopurinol on total body urates, uric acid analyses were conducted at various developmental times; the results are found in Table 4. It is apparent by examining this table that uric acid accumulates with age in normal German cockroaches. Nymphs fed allopurinol bait fail to accumulate appreciable amounts of uric acid. Males (1-4 days old) fed allopurinol as nymphs had only 8.87 µg/mg dry weight, whereas their normal counterparts, at 1-7 days of age, had 88.4 µg/mg dry weight. Females (30 days old) had an analogous pattern (exposed females had 9.79 µg/mg dry weight and normal females had 123.9 µg/mg dry weight). Feeding allopurinol to 14 day-old postemergent adults did not deplete the amount of total body urates when compared to unexposed adults of similar age (30 days old).

TABLE 4

Comparison of the mean uric acid content of German cockroaches fed allopurinol bait as nymphs and various stages of unexposed specimens

| Sex | Mean Uric Acid Content (µg/g dry wt) | |
| --- | --- | --- |
|  | Males | Females |
| Treatment Unexposed |  |  |
| Penultimate nymphs | 66.10c | 91.80c |
| 1-day old adults | 106.30b | 83.10c |
| 1-7 day old adults | 88.40bc | 91.00c |
| 30-day old adults | 161.10a | 123.90b |
| Allopurinol Treated |  |  |
| 1-4 day old adults | 8.87d | — |
| 30-day old adults | — | 9.79d |
| 30-day old adults fed bait 14 days postemergence | 161.30a | 133.90a |

Means within a column followed by the same letter were not significantly different (P = 0.05; Waller-Duncan Method [SAS Institute, 1985]).

Allopurinol's ability to inhibit the deposition of uric acid is apparently the key to disruption of homeostasis and reproduction. Nymphs fed a 2% allopurinol laboratory rodent chow bait in either a choice or nonchoice situation experienced ca. 1 week delay in adult emergence, reduced survival (2-7%) at 10-12 weeks and reproductive failure. Combining the bait treatment with a 0.1% hydroprene residual caused no significant change in these findings. Postemergent adults fed the 2% bait experienced a significant reduction in the number of nymphs produced per exposed female.

The reduction (ca. 10×) in whole body urates, the reduced longevity of emergent adults, particularly males (1-7 days), and the absence of reproduction seem to underscore the importance of this metabolic reserve.

EXAMPLE 5

Several formulations having the compositions set forth in Table 5 were prepared and tested against German cockroaches as described above in Example 1. The survival rates are set forth in Table 5.

TABLE 5

Percent survival of cockroaches fed various dosages of allopurinol-treated bait

| Week posttreatment | Untreated | Percent allopurinol in bait | | | | |
| --- | --- | --- | --- | --- | --- | --- |
|  |  | 2% | 0.1% | 0.05% | 0.01% | 0.001% |
| 1 | 95.56 | 98.89 | 98.89 | 98.89 | 98.89 | 97.78 |
| 2 | 95.56 | 94.44 | 95.56 | 97.78 | 95.56 | 96.67 |
| 3 | 94.44 | 90.00 | 91.11 | 92.22 | 94.44 | 95.56 |
| 4 | 92.22 | 86.67 | 84.44 | 83.33 | 93.33 | 94.44 |
| 5 | 91.11 | 83.33 | 70.00 | 73.33 | 93.33 | 94.44 |
| 6 | 90.00 | 80.00 | 41.11 | 60.00 | 92.22 | 93.33 |
| 7 | 90.00 | 76.67 | 26.67 | 37.78 | 93.33 | 93.33 |
| 8 | 90.00 | 70.00 | 6.67 | 21.11 | 93.33 | 93.33 |
| 9 | 90.00 | 67.78 | 2.22 | 16.67 | 93.33 | 93.33 |
| 10 | 90.00 | 52.22 | 0.00 | 14.44 | 93.33 | 93.33 |
| 11 | 90.00 | 45.56 | 0.00 | 12.22 | 93.33 | 93.33 |
| 12 | 88.89 | 32.22 | 0.00 | 10.00 | 93.33 | 93.33 |
| 13 | 88.89 | 15.56 | 0.00 | 7.78 | 92.22 | 93.33 |
| 14 | 88.89 | 8.89 | 0.00 | 6.67 | 92.22 | 93.33 |
| 15 | 87.78 | 7.78 | 0.00 | 5.56 | 90.00 | 92.22 |

We claim:

1. A method for regulating the growth and mortality of cockroaches comprising administering thereto a cockroach growth regulating and mortality effective amount of allopurinol for a period of time of at least 3 weeks to affect the growth and mortality thereof.

2. The method of claim 1 for the regulation of the growth of German Cockroaches, *Blattella germanica* L.

3. The method of claim 1 wherein said allopurinol is administered by incorporation in a bait or attractant for cockroaches which is ingested by said cockroaches.

4. The method of claim 3 wherein said bait or attractant contains from about 0.5% to about 2.0%, by weight, of allopurinol.

5. The method of claim 1 wherein said allopurinol is administered to said cockroaches for a period of time of at least about 5 weeks.

6. The method of claim 1 including co-administering to said cockroaches with said allopurinol a toxic amount of a cockroach insecticide.

* * * * *